United States Patent
Zrein

(10) Patent No.: US 6,458,922 B1
(45) Date of Patent: Oct. 1, 2002

(54) ANTIGENS AND IMMUNOASSAYS FOR DIAGNOSING CHAGAS' DISEASE

(75) Inventor: Maan Zrein, Bondues (FR)

(73) Assignee: Innogenetics N.V. (BE)

(*) Notice: Subject to any disclaimer, the term of this patent is extended or adjusted under 35 U.S.C. 154(b) by 0 days.

(21) Appl. No.: 09/356,778

(22) Filed: Jul. 16, 1999

(30) Foreign Application Priority Data

Jul. 30, 1998 (EP) .............................. 98870166

(51) Int. Cl.$^7$ ...................... A61K 38/00; A61K 39/002; C07K 1/00; G01N 33/569; G01N 33/53

(52) U.S. Cl. ...................... 530/300; 530/350; 530/822; 530/806; 435/7.22; 435/975; 424/269.1; 424/265.1; 424/266.1; 424/185.1

(58) Field of Search ................................ 530/300, 350, 530/822, 820, 806; 424/191.1, 269.1, 265.1, 266.1, 185.1; 435/7.22, 810, 975

(56) References Cited

U.S. PATENT DOCUMENTS 5,916,572 A * 6/1999 Reed et al. .............. 424/269.1

FOREIGN PATENT DOCUMENTS

| WO | WO9525797 | * | 9/1995 |
| WO | 9718475 | | 5/1997 |

OTHER PUBLICATIONS

Houghten et al. Vaccine86, Cold Spring Harbor Laboratory, pp. 21–25, 1986.*
Lorca et al. Revista Medica De Chile 121: 363–368, 1993, abstract.*
Engman et al. J. Biol. Chem. 264: 18627–18631, 1989.*
Lafaille et al. Mol. Biochem. Parasitol. 35: 127–136, 1989.*
Cotrim et al. J. Clin. Microbiol. 28: 519–524, 1990.*
Burns et al. PNAS 89: 1239–1243, 1992.*
Ibanez et al. Mol. Biochem. Parasitol. 30: 27–34, 1988.*
Pollevick et al. Mol. Biochem. Parasitol. 47:247–250, 1991.*
Buschiazzo et al. Mol. Biochem. Parasitol. 54: 125–128, 1992.*
Almeida et al. Mem. Inst. Oswaldo Cruz. 85: 513–517, 1990.*
Pastini, et al., "Immunoassay . . . Chagas Disease", Clin. Chem., vol. 40, No. 10, 1994, pp. 1893–1897.
Vergara et a;. "Assay . . . Synthetic Peptides", J. Clin. Microbiol., vol. 29, No. 9, 1991, pp. 2034–2037.

* cited by examiner

Primary Examiner—S. Devi
(74) Attorney, Agent, or Firm—Bierman, Muserlian and Lucas

(57) ABSTRACT

Transfusion of contaminated blood has become the major route of transmission for Chagas' disease. Current screening tests are insensitive and yield conflicting results, while confirmatory assays do not exist. The present invention relates to antigens and their use for serological diagnosis of Chagas' disease. More specifically, the present invention concerns assays which are able to reliably and accurately detect the presence of antibodies to various specific antigens of *Trypanosoma cruzi* in a highly sensitive and specific manner.

4 Claims, 2 Drawing Sheets

FIG. 1

Figure 2:
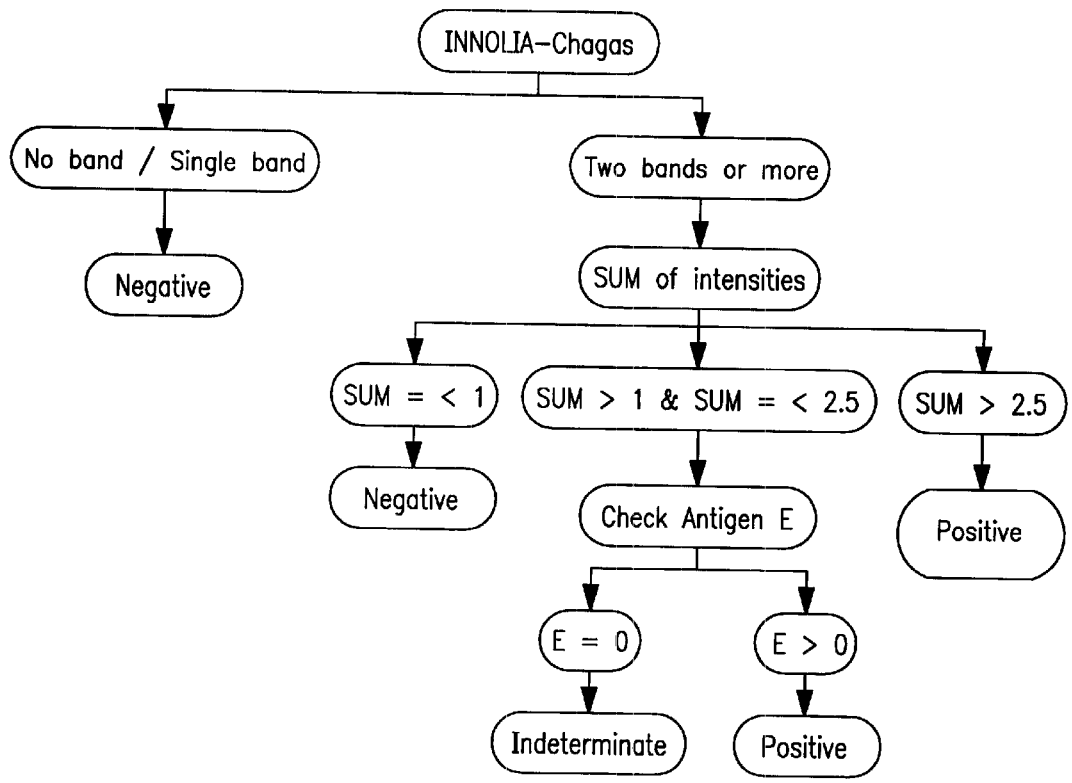

| serum# | strip# | antigens (control -/+, 1+, 3+, sv / A B C D E F G) | SV | A | B | C | D | scores E | F | G | E | LIA result |
|---|---|---|---|---|---|---|---|---|---|---|---|---|
| C+ | 1 | | SV | 1 | 2 | 1 | 3 | 3 | 0,5 | 4 | 14.5 | + |
| C− | 2 | | − | − | − | − | − | − | − | − | − | N |
| VL3 | 3 | | − | 0,5 | 3 | 0,5 | 0,5 | 2 | − | 4 | 10.5 | + |
| VL6 | 4 | | − | 1 | 2 | 0,5 | 4 | 3 | 0,5 | 4 | 15 | + |
| VL10 | 5 | | − | 0,5 | 0,5 | − | 1 | 2 | 1 | 3 | 8 | + |
| VL16 | 6 | | − | 1 | − | − | 2 | 2 | − | 3 | 8 | + |
| VL59 | 7 | | − | 0,5 | − | − | 3 | 4 | − | 2 | 9.5 | + |
| PI8798 | 8 | | − | 2 | 0,5 | − | 1 | − | − | 2 | 5.5 | + |
| PI8807 | 9 | | − | − | − | − | 2 | 1 | 0,5 | − | 3.5 | + |
| PI8810 | 10 | | − | 0,5 | − | − | − | 2 | − | 2 | 4.5 | + |
| PI8864 | 11 | | − | − | − | − | − | − | 0,5 | − | 0.5 | N |
| PI8895 | 12 | | − | − | 1 | 0,5 | − | − | − | − | 1.5 | N |
| PB6 | 13 | | − | − | − | − | − | 0,5 | − | 0,5 | 0.5 | N |
| PB7 | 14 | | − | − | − | − | − | 0,5 | − | − | 1.5 | + |
| AM10.1 | 15 | | − | 0,5 | − | − | − | 1 | − | − | 1.6 | + |
| AM51.5 | 16 | | − | − | − | − | − | − | 1 | 1 | 1 | N |
| PB97 | 17 | | − | − | − | − | − | 1 | 0,5 | 2 | 3.5 | + |
| PB122 | 18 | | − | − | − | − | − | − | 0,5 | − | 1.5 | + |
| PB140 | 19 | | − | − | − | − | 0,5 | − | − | 1 | 1.6 | ind |
| PB19 | 20 | | − | − | − | − | − | 0,5 | − | 2 | 2 | N |
| PB323 | 21 | | − | 0,5 | − | − | − | 2 | − | 1 | 3.5 | + |
| PB155 | 22 | | − | 0,5 | − | − | − | 3 | − | 2 | 6.6 | + |
| PB167 | 23 | | − | − | − | − | − | − | 3 | − | 3 | N |
| PB168 | 24 | | − | 0,5 | − | − | 0,5 | − | 0,5 | 3 | 4.5 | + |
| PB170 | 25 | | − | − | − | − | − | 0,5 | − | 2 | 2.5 | + |
| PB197 | 26 | | − | − | − | − | − | 3 | 1 | 4 | 8 | + |

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 211 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 1:

```
Met Gly Ala Cys Gly Ser Lys Gly Ser Thr Ser Asp Lys Gly Leu Ala
 1               5                  10                  15

Ser Asp Lys Asp Gly Lys Lys Ala Lys Asp Arg Lys Glu Ala Trp Glu
            20                  25                  30

Arg Ile Arg Gln Ala Ile Pro Arg Glu Lys Thr Ala Glu Ala Lys Gln
        35                  40                  45

Arg Arg Ile Glu Leu Phe Lys Lys Phe Asp Lys Asn Glu Thr Gly Lys
    50                  55                  60

Leu Cys Tyr Asp Glu Val His Ser Gly Cys Leu Glu Val Leu Lys Leu
65                  70                  75                  80

Asp Glu Phe Thr Pro Arg Val Arg Asp Ile Thr Lys Arg Ala Phe Asp
                85                  90                  95

Lys Ala Arg Ala Leu Gly Ser Lys Leu Glu Asn Lys Gly Ser Glu Asp
            100                 105                 110

Phe Val Glu Phe Leu Glu Phe Arg Leu Met Leu Cys Tyr Ile Tyr Asp
        115                 120                 125

Phe Phe Glu Leu Thr Val Met Phe Asp Glu Ile Asp Ala Ser Gly Asn
   130                  135                 140

Met Leu Val Asp Glu Glu Leu Lys Arg Ala Val Pro Lys Leu Glu
145                 150                 155                 160

Ala Trp Gly Ala Lys Val Glu Asp Pro Ala Ala Leu Phe Lys Glu Leu
                165                 170                 175

Asp Lys Asn Gly Thr Gly Ser Val Thr Phe Asp Glu Phe Ala Ala Trp
            180                 185                 190

Ala Ser Ala Val Lys Leu Asp Ala Asp Gly Asp Pro Asp Asn Val Pro
        195                 200                 205

Glu Ser Ala
    210
```

(2) INFORMATION FOR SEQ ID NO: 2:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 2:

```
Val Ala Glu Ala Glu Lys Gln Lys Ala Ala Glu Ala Thr Lys Val Ala
 1               5                  10                  15

Glu Ala Glu Lys Gln Lys Ala Ala Glu Ala Met Lys
```

```
                20                  25
```

(2) INFORMATION FOR SEQ ID NO: 3:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 3:

```
Met Glu Gln Glu Arg Arg Gln Leu Leu Glu Lys Asp Pro Arg Arg Asn
1               5                   10                  15

Ala Arg Glu Ile Ala Ala Leu Glu
                20
```

(2) INFORMATION FOR SEQ ID NO: 4:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 4:

```
Gly Ala Glu Pro Lys Ser Ala Glu Pro Lys Pro Ala Glu Pro Lys Ser
1               5                   10                  15

Ala Glu Pro Lys Pro
                20
```

(2) INFORMATION FOR SEQ ID NO: 5:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 5:

```
Ala Leu Pro Gln Glu Gln Glu Asp Val Gly Pro Arg His Val Asp
1               5                   10                  15

Pro Asp His Phe Arg Ser Thr Thr Gln Asp Ala Tyr Arg Pro Val Asp
                20                  25                  30

Pro Ser Ala Tyr Lys Arg
        35
```

(2) INFORMATION FOR SEQ ID NO: 6:

(i) SEQUENCE CHARACTERISTICS:
        (A) LENGTH: 24 amino acids

```
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 6:

Asp Ser Thr Ala His Gly Thr Pro Ser Thr Pro Ala Asp Ser Ser Ala
1               5                  10                  15

His Ser Thr Pro Ser Thr Pro Ala
            20

(2) INFORMATION FOR SEQ ID NO: 7:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 7:

Pro Ser Pro Phe Gly Gln Ala Ala Ala Gly Asp Lys Pro Ser Pro Phe
1               5                  10                  15

Gly Gln Ala Ala Ala Gly Asp Lys
            20
```

ANTIGENS AND IMMUNOASSAYS FOR DIAGNOSING CHAGAS' DISEASE

FIELD OF THE INVENTION

The present invention relates generally to sets of at least 6 recombinant and/or synthetic peptides derived from *Trypanosoma cruzi* proteins which are used for diagnosing Chagas' disease in a highly sensitive and specific manner. More specifically, the present invention relates to peptides derived from the *T. cruzi* antigens SAPA, CRA, FRA, TcD, Tc24, Ag39 and MAP which are used in a confirmatory immunoassay and concerns kits comprising the latter peptides.

BACKGROUND OF THE INVENTION

Chagas' disease is endemic throughout Latin America and a major cause of morbidity and mortality in those countries affected. Approximately 16–18 million people are infected, and about 50,000 patients die each year from the condition (Carvalho et al., 1993). Its etiologic agent, the protozoan parasite *Trypanosoma cruzi,* is naturally transmitted by various species of triatomine bugs. Disease transmission occurs when infectious forms of the parasite are deposited during the blood meal along with the insect's feces. In Brazil, successful vector control programs have almost completely abolished naturally occurring transmission, with the exception of the hinterland. As a result, transfusion of blood from infected donors—often migrants to larger cities—has become the major route for contracting the parasite (Almeida et al., 1990). Recent surveys estimate the annual number of transfusion-acquired Chagas' disease cases in Brazil at 20,000 out of a total of 5 to 6 million blood transfusions (Zingales et al., 1990). Consequently, an efficient donor screening program is crucial in eliminating contaminated blood while not negatively affecting the country's blood supply.

In Brazilian blood banks, the screening for antibodies directed against *T. cruzi* is mandatory. Screening assays include indirect immunofluorescence (IFA), indirect hemagglutination (IHA), and enzyme-linked immunosorbent assays (ELISA). The utilization of at least two assays based on either different methodologies or different antigen preparations is currently recommended, but conflicting results are often observed. A few specialized laboratories have developed Western blot techniques (Peralta et al., 1994) in an attempt to resolve discrepant results, but no single test is sufficiently sensitive to prevent transfusion transmission of Chagas' disease.

Most of the tests that are commercially available today employ crude parasite extracts or subcellular fractions as antigen preparations. However, it has been shown that parasite extracts cross-react with sera from patients harboring other diseases such as leishmaniasis, *Trypanosoma rangeli* infection, syphilis, or rheumatic fever. In recent years, various investigators have reported the cloning and characterization of *T. cruzi*-specific immunoreactive antigens (Borges-Pereira, 1997). Several studies have evaluated the diagnostic potential of these recombinant antigens either in the form of fusion proteins or as synthetic peptides (Almeida et al., 1990; Peralta et al., 1994). Although an increase in sensitivity and specificity of these assays was observed, cross-reactivity with Leishmania-specific antibodies still occurred. The present invention relates to sets of at least 6 recombinant and/or synthetic peptides derived from *Trypanosoma cruzi* antigens which are used for diagnosing Chagas's disease in a highly sensitive and specific manner and which do not cross react with Leishmania-specific antibodies. The use of a new multiparameter assay combining relevant and immunodominant antigens derived from *T. cruzi* proteins as a diagnostic test for Chagas' disease is herein described.

AIMS OF THE INVENTION

It is clear from the above that no single test is sufficiently sensitive to prevent transfusion transmission of Chagas' disease which has become the major route of transmission for this infection. Current screening tests are insensitive, non-specific and yield conflicting results, while convenient confirmatory assays do not exist. The present invention therefore aims at providing sets of recombinant and/or synthetic antigens and their use for serological diagnosis of Chagas' disease. More specifically, the present invention aims at providing assays which are able to reliably and accurately detect the presence of antibodies to various specific antigens of *Trypanosoma cruzi* in a highly sensitive and specific manner. In this regard, the present invention aims at providing sets of at least 6 recombinant and/or synthetic peptides derived from the *T. cruzi* antigens SAPA, CRA, FRA, TcD, Tc24, Ag39 and MAP for usage in a confirmatory immunoassay and aims at providing kits comprising the latter peptides. Moreover, it is also an aim of the present invention to provide sets of *T. cruzi* antigens which can be used in a vaccine composition for immunizing an individual to prevent Chagas' disease upon exposure to *T. cruzi*.

BRIEF DESCRIPTION OF TABLES AND DRAWINGS

Table 1 shows a comparison of the results obtained from analysing 1062 sera with the INNO-LIA Chagas Ab assay with the results obtained from analysing the same set of sera with four different screening assays: an in-house ELISA and three commercial enzyme immunoassays (see Examples section).

Table 2 shows typical reactivity-patterns of 57 serum samples (serial numbers 1 to 57 and corresponding serum are given in the identification columns) on the INNO-LIA Chagas. The peptides used in the INNO-LIA Chagas are indicated by the letters A to G (A=SEQ ID N° 1; B=SEQ ID 2; C=SEQ ID 3; D=SEQ ID 4; E=SEQ ID 5; F=SEQ ID 6; G=SEQ ID 7). The scores are given for each antigen line ranging from 0 to 4 (see columns 4 to 10 and see also Examples section). The final interpretation is compared with the number of positive results (0 to 4, screening column) obtained by analysing the same sera with four different screening assays as indicated-above.

Table 3 shows the amino acid sequence (one-letter code) of the seven peptides used in the INNO-LIA Chagas and their corresponding SEQ ID numbers.

FIG. 1 illustrates representative INNO-LIA Chagas Ab results on 26 serum samples (serum ID is indicated in column 1) and their respective interpretations (see Examples section). The peptides (antigens) used in the INNO-LIA Chagas are indicated by the letters A to G (A=SEQ ID N° 1; B=SEQ ID 2; C=SEQ ID 3; D=SEQ ID 4; E=SEQ ID 5; F=SEQ ID 6; G=SEQ ID 7). N=negative result; ind= indeterminate; +=positive result.

FIG. 2 depicts the algorithm which was established based on the reactivity in the four ELISA screening assays and the reactivity pattern in the INNO-LIA Chagas Ab (see Examples section):

DETAILED DESCRIPTION OF THE INVENTION

The invention described herein draws on previously published work and pending patent applications. By way of example, such work consists of scientific papers, patents or pending patent applications. All these publications and applications, cited previously or below are hereby incorporated by reference.

The present invention concerns a composition comprising at least 6 recombinant and/or synthetic peptides which bind to Trypanosoma cruzi-specific antibodies and do not bind to Leishmania-specific antibodies. The term "at least 6" indicates that the present invention concerns a composition comprising 6, 7, 8, 9, 10, 11, 12 or more peptides which bind to Trypanosoma cruzi-specific antibodies and do not bind to Leishmania-specific antibodies: It should be clear that any combination of at least 6 peptides which are functionally defined by their binding to Trypanosoma cruzi-specific antibodies and their "not-binding" to Leishmania-specific antibodies fall within the scope of the present invention. As an example of the latter combination, which is not intended to limit the scope of the present invention, the present invention specifically relates to a composition comprising 7 recombinant and/or synthetic peptides which bind to Trypanosoma cruzi-specific antibodies and do not bind to Leishmania-specific antibodies and which are derived from the T. cruzi antigens chosen from the group consisting of the well-characterized SAPA, CRA, FRA, TcD, Tc24, Ag39 and MAP proteins (see Table 3 and see also further). In other words, it should be clear that the latter composition is a preferred embodiment of the present invention but that any other related composition comprising at least 6 peptides derived from the latter proteins and/or from proteins such as Ag1 and Ag2 (disclosed in WO91/15584 to Goldenberg et al.), Tc100 (disclosed in WO96/05312 to Paranhos Baccala et al.), Gp90, Gp60/50 and LPPG (disclosed in WO94/01776 to Winkler et al.), TCR27 (disclosed in WO95/25797 to Kirchoff and Otsu), TcE and PEP2 (disclosed in WO 96/29605 and WO97/18475 to Reed and Reed et al., respectively), Ag 13 and Ag 30 (disclosed in Pastini et al., 1994) or any other protein known in the art which bind to Trypanosoma cruzi-specific antibodies and do not bind to Leishmania-specific antibodies are also part of the present invention.

The terms "recombinant and/or synthetic peptides" relate to peptides (i.e. polymers of generally fewer than about 50 amino acids-except for the recombinant peptide Tc24 which contains 211 amino acids (see table 3)-) generated using any technique well known to those of ordinary skill in the art such as recombinant DNA techniques as described by Maniatis et al. (1982) and in WO96/29605 to Reed and classical chemical synthesis as described by Houbenweyl (1974), Atherton and Shepard (1989), and in WO96/29605 to Reed.

The terms "which bind to Trypanosoma cruzi-specific antibodies and do not bind to Leishmania-specific antibodies" refer to combinations of at least 6 peptides as defined above which reliably, accurately and specifically detect the presence of antibodies to various antigens of the species Trypanosoma cruzi in a biological sample and do not cross-react with antibodies to antigens of species belonging to the genus Leishmania—especially to Leishmania-species which cause visceral or tegumentary leishmaniasis—possibly present in the same biological sample. The term "cross-react" used herein refers to the reaction (i.e. the binding) of one antigen (i.e. a peptide derived from a T. cruzi protein) with antibodies developed against another antigen (i.e. a Leishmania-species antigen). Moreover, it should be clear that the composition of the present invention does preferably not cross-react to antigens of other species belonging to the genus Trypanosoma such as T. rangeli or to antigens of species belonging to the genera Plasmodium, Treponema and/or Mycobacterium.

As already mentioned above, the present invention specifically relates to a composition as defined above, wherein said peptides are derived from the T. cruzi antigens chosen from the group consisting of SAPA (disclosed in Pollevick et al.,1991 and Vergara et al. 1992), CRA and FRA (disclosed in Lafaille et al., 1989), TcD (disclosed in Burns et al., 1992 and Peralta et al., 1994), Tc24 (disclosed in Guevara et al., 1997 and FR 2692900 to Taibi et al.), Ag39 (Hoft et al., 1989) and MAP (Kerner et al., 1991) proteins.

Furthermore, the present invention concerns a composition as defined above wherein said peptides have amino acid sequences given by SEQ ID N° 1 to 7 (see Table 3) or any variant thereof. As used herein, the term "variant" refers to a peptide which differs from the recited peptides having SEQ ID N° 1, 2, 3, 4, 5, 6 or 7 only in conservative substitutions or modifications such that it retains the binding properties of the recited peptides. A "conservative substitution" is one in which an amino acid is substituted for another amino acid that has similar properties, such that one skilled in the art of peptide chemistry would expect the secondary structure and hydropathic nature of the peptide to be substantially unchanged. Variants may also, or alternatively, contain other conservative modifications, including the deletion or addition of amino acids that have minimal influence on the binding properties, secondary structure or hydropathic nature of the peptide. For example, the peptide may be conjugated to a linker or other sequence for ease of synthesis or to enhance binding of the peptide to a solid support. Also included within the definition are post-translational modifications of the peptides represented by SEQ ID 1 to 7 such as glycosylation, acetylation, phosphorylation, modifications with fatty acids and the like, peptides containing disulfide bounds between cysteine residues, biotinylated peptides as well as other modifications known in the art.

The present invention further relates to a method for detecting the presence of T. cruzi antibody in a biological sample, comprising:
  contacting said biological sample with the peptides of the composition as defined above, and
  detecting in a biological sample the presence of antibodies that bind to the peptides of the composition as defined above.

The terms "a method for detecting" refer to any immunoassay known in the art such as assays which utilize biotin and avidin or streptavidin (such as LIA's), ELISA's and immunoprecipitation and agglutination assays. A detailed description of these assays is given in WO96/13590 to Maertens and Stuyver, Zrein et al. (1998) and WO96/29605 to Reed which are incorporated herein by reference.

The term "biological sample" refers to a fluid obtained from an organism such as serum, plasma, saliva, gastric secretions, mucus and the like. More specifically, the latter term refers to a human serum sample. The term "T. cruzi antibody" refers to any polyclonal or monoclonal antibody binding to a T. cruzi protein. More specifically the latter term refers to any polyclonal or monoclonal VI antibody binding to the T. cruzi proteins SAPA, CRA, FRA, TcD, Tc24, Ag39, MAP, Ag1, Ag2, Tc100, Gp90, Gp60/50, LPPG, TCR27, TcE, PEP2, Ag 13 or Ag 30 (see above). The term is not limiting regarding the species or source of the antibody, nor is intended to be limited by the manner in which it is made. In addition, the term "antibody" also refers to humanized antibodies as described in U.S. Pat. No. 4,946,778 and to fragments of antibodies which retain the antigen binding function and specificity of the parent antibody.

Moreover, the present invention relates to a method as defined above wherein the step of detecting comprises:
  removing unbound sample,
  adding a detection reagent, and
  determining the level of reacting antibodies relative to a predetermined cutoff value.

The term "detection reagent" refers to any compound that binds to the peptide-*T. cruzi* antibody complex formed after contacting said biological sample with the peptides of the composition as defined above and that can be detected by any of a variety of means known to those in the art. Preferably, the detection reagent contains a binding agent (such as for example Protein A, Protein G, immunoglobulin, lectin or free antigen) conjugated to a reporter group including enzymes, substrates, cofactors, inhibitors, dyes, radioactive groups, luminescent groups, fluorescent groups and biotin. The conjugation of binding agent to reporter group may be achieved using standard methods known to those skilled in the art. The terms "determining the level of reacting antibodies relative to a predetermined cutoff value" relate to the determination of the presence or absence of *T. cruzi* antibodies in the sample by detecting the signal obtained from the reporter group (methods to detect the latter signal are described for in detail in WO 96129606 to Reed) which is compared to a signal that corresponds to a predetermined cut-off value. This cut-off value is often the average mean signal obtained when the peptides are incubated with samples from an uninfected patient (see also the Examples section).

Furthermore, the present invention relates to a method as defined above wherein said peptides of the composition as defined above are bound to a solid support. Examples of such solid supports are nylon, nitrocellulose, latex, dextran, gold and/or a plastic material.

Furthermore, the present invention also relates to a method as defined above wherein said peptides of the composition as defined above are bound to a solid support in a line-wise fashion. More specifically, the latter method refers to an immunoassay as described in detail by Zrein et al. (1998).

Of course, numerous other method- and assay protocols exist that are suitable for use with the peptides of the present invention. The above descriptions are intended to be exemplary only.

The present invention also relates to a diagnostic kit for detecting *T. cruzi* infection in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

A final embodiment of the present invention is the usage of the peptides as defined above in a vaccine composition. The term "a vaccine composition" relates to an immunogenic composition capable of eliciting protection against *T. cruzi* infection, whether partial or complete. The peptides of the present invention can be used as such, in a biotinylated form (as explained in WO 93/18054) and/or complexed to Neutralite Avidin according to the manufacturer's instruction sheet (Molecular Probes Inc., Eugene, Oreg.). It should also be noted that "a vaccine composition" comprises, in addition to an active substance (i.e. the peptides of the present invention), a suitable excipient, diluent, carrier and/or adjuvant which, by themselves, do not induce the production of antibodies harmful to the individual receiving the composition nor do they elicit protection. Suitable carriers are typically large slowly metabolized macromolecules such as proteins, polysaccharides, polylactic acids, polyglycolic acids, polymeric aa's, aa copolymers and inactive virus particles. Such carriers are well known to those skilled in the art.

Preferred adjuvants to enhance effectiveness of the composition include, but are not limited to: aluminum hydroxide, aluminum in combination with 3-0 deacylated monophosphoryl lipid A as described in WO 93/19780, aluminum phosphate as described in WO 93/24148, N-acetyl-muramyl-L-threonyl-D-isoglutamine, as described in U.S. Pat. No. 4,606,918, N-acetyl-normuramyl-L-alanyl-D-isoglutamine, N-acetylmuramyl-L-alanyl-D-isoglutamyl-L-alanine 2 (1'dipalmitoyl-sn-glycero-3-hydroxyphosphoryloxy) ethylamine and RIBI (ImmunoChem Research Inc., Hamilton, Mont.) which contains monophosphoryl lipid A, detoxified endotoin, trehalose-6,6-dimycolate, and cell wall skeleton (MPL+ TDM+CWS) in a 2% squalene/TWEEN 80/ emulsion. Any of the three components MPL, TDM or CWS may also be used alone or combined 2 by 2. Additionally, adjuvants such as Stimulon (Cambridge Bioscience, Worchester, Mass.) MF 57 (Chiron) or SAF-1 (Syntex) may be used. Furthermore, Complete Freund's Adjuvant (CFA) and Incomplete Freund's Adjuvant (IFA) may be used for non-human applications and research purposes.

A vaccine composition "will further contain excipients and diluents, which are inherently non-toxic and non-therapeutic, such as water, aline, glycerol, ethanol, wetting or emulsifying agents, pH buffering substances, preservatives, and the like. Typically, a vaccine composition is prepared as an injectable, either as a liquid solution or suspension. Solid forms, suitable for solution on, or suspension in, liquid vehicles prior to injection may also be prepared. The preparation may also be emulsified or encapsulated in liposomes for enhancing adjuvant effect. The polypeptides may also be incorporated into Immune Stimulating Complexes together with saponins, for example Quil A (ISCOMS)

Vaccine compositions comprise an immunologically effective amount of the peptides of the present invention, as well as any other of the above-mentioned components. "Immunologically effective amount" means that the administration of that amount to an individual, either in single doses or as part of a series, is effective for prevention or treatment. This amount varies depending upon the health and physical condition of the individual to be treated, the taxonomic group of the individual to be treated (e.g. non-human primate, primate, etc.), the capacity of the individual's immune system to mount an effective immune response, the degree of protection desired, the formulation of the vaccine, the treating's doctor assessment, the strain of the infecting parasite and other relevant factors. It is expected that the amount will fall in a relatively broad range that can be determined through routine trials. Usually, the amount will vary from 0.01 to 1000 μg/dose, more particularly from 0.1 to 100 μg/dose.

The vaccine compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents. It should be noted that a vaccine may also be useful for treatment of an individual, in which case it is called a "therapeutic vaccine".

The present invention will now be illustrated by reference to the following examples which set forth particularly advantageous embodiments. However, it should be noted that these embodiments are illustrative and can not be construed as to restrict the invention in any way.

EXAMPLES

Evaluating a recombinant and peptide antigen line immunoassay for Chagas' disease: the INNO-LIA Chagas Antibody (Ab) assay a. Materials and Methods Study Population The 1062 sera employed in this retrospective study were obtained from patients and healthy residents of four Brazilian regions endemic for Chagas' disease: 261 sera were from the state of Minas Gerais (municipality Virgem da Lapa) where the cardiac and digestive forms of the disease are frequent; 465 and 253 sera were obtained in the hinterlands of Paraiba and Piaui, respectively, where the indeterminate form of the disease is common; and 83 sera were from the Amazon (municipality of Barcellos) where Chagas' disease is emerging. Most of the blood samples originated from patients who have been participating in long-term follow-up studies for 2–20 years. Serologic analysis was performed using several immunological methods (see below). In addition, the presence of the parasite could be demonstrated in some patients by xenodiagnosis and/or PCR.

Sera from patients with visceral leishmaniasis (n=20) were obtained in Natal, State of Rio Grande do Norte, Brazil. Serologic diagnosis was performed using a dot ELISA, and the parasites were isolated from material obtained by bone marrow puncture. Sera from patients with tegumentary leishmaniasis (n=20) originated in Macaé, State of Rio de Janeiro, Brazil. The patients were diagnosed by histopathologic examination of biopsies, and the parasites were isolated by culture of material obtained from the lesions.

Serologic Characterization

All sera were serologically characterized by four different screening assays: an in-house and three commercial ELISAs, as described further and in Oelemann et al. (1998). These four assays were used to establish an interpretation algorithm for the evaluation of the INNO-LIA Chagas Ab.

For the in-house ELISA, the cytosolic fraction of *T. cruzi* strain Y epimastigotes was used as antigen, and sera were tested at a 1/200 dilution. After incubation with anti-human IgG-peroxidase conjugate, the immune complexes were developed with TMB/$H_2O_2$ (Sigma, St. Louis, Mo.) and absorbencies read at 450 nm. Cut-off values were empirically determined by dividing the difference of the average absorbencies of two positive and three negative controls by three ([Av positive–Av negative]/3).

Commercial enzyme immunoassays included the Abbott Chagas antibody EIA (Abbott Laboratorios do Brasil, São Paulo, Brazil), the BIOELISACRUZI® (Biolab-Mérieux, Rio de Janeiro, Brazil), and the BIOZIMA Chagas (Polychaco S.A.I.C, Buenos Aires, Argentina). All tests were carried out according to the instructions provided by the manufacturers.

All of these sera had also been tested at a final dilution of 1/40 with either a commercial or an in-house IFA tests according to Camargo (1966) using *T. cruzi* strain Y epimastigotes as antigen and FITC-conjugated goat anti-human IgG (Cappel Biomedical Inc., Malven, Pa.). In addition, some sera were characterized by an in-house Western blot, as described previously (Peralta et al., 1994). Briefly, the cytosolic fraction of *T. cruzi* epimastigotes (Y strain) was submitted to SDS-PAGE in 10% acrylamide gels and subsequently transferred to nitrocellulose membranes. Diluted serum samples (1/100) were then added to the membranes, and the immune complexes formed were revealed using anti-human IgG-peroxidase conjugate followed by a color reaction. Sera were considered positive when they reacted with at least 3 bands from a group of seven (14-, 19-, 27-, 30-, 34-, 37-, and 75 kDa).

The INNO-LIA Chagas Ab Assay

The INNO-LIA Chagas Ab assay consists of seven recombinant and synthetic *T. cruzi* antigens coated as discrete lines onto a nylon membrane with plastic backing. In addition, the strips contain control lines for sera with strong, moderate, and weak (cut-off) reactivity, and a streptavidin background control. The antigens were derived from the sequences of the following recombinant antigens described in the literature: Ag 39 (Hoft et al., 1989), TcD (Burns et al., 1992), Tc24 (FR 2692900 to Taibi et al.), SAPA (Pollevick et al., 1991), MAP (Kerner et al., 1991), CRA (Lafaille et al., 1989), and FRA (Lafaille et al., 1989). The strips were incubated with the sera at a 1/100 dilution for 18 hours at 25° C. and, after washing, the immune complexes were detected by incubation with an anti-human IgG conjugate and subsequent color development. Results were determined by visually comparing the intensities of the antigen lines with those of the controls. The intensities were scored as follows: 0 (–), absent or less intense than the cut-off line; 0.5 (±), intensity higher than or equal to that of the cut-off line but lower than the 1+ control line; 1 (+), intensity equal to that of the 1+ control line; 2 (++), intensity between that of the 1+ control line and of the 3+ control line; 3 (+++), intensity equal to that of the 3+ control line; 4 (++++), intensity higher than that of the 3+ control line. The INNO-LIA results can thereby be expressed as a numeric value, i.e., the sum of intensities of the different antigen bands. FIG. 1 shows representative INNO-LIA results and their respective interpretations.

Based on the reactivity in the four ELISA screening assays and the reactivity pattern with the multiple antigens used in the INNO-LIA Chagas Ab, an algorithm was established (FIG. 2). Those study samples for which the four screening assays employed were either all positive (thus considered as true-positive samples; n=500) or all negative (considered as true-negative samples; n=460) were selected to define an INNO-LIA interpretation algorithm. The algorithm illustrated in FIG. 2 was optimized for sensitivity and specificity based on this subset of samples. The remaining samples (n=102) with conflicting ELISA results were then classified using the established algorithm as being INNO-LIA-negative, INNO-LIA-positive, or INNO-LIA-indeterminate.

Statistical Methods

The GraphPad StatMate™ software (version 1.01, San Diego, Calif.) was used for the calculation of 95% confidence intervals (CI) for proportions.

b. Results and Discussion

Evaluation of INNO-LIA Chagas Ab Assay Using Chagasic Sera

In order to evaluate the performance of the INNO-LIA Chagas Ab assay, we analyzed 1062 sera and compared the results with those obtained in four different screening assays, an in-house ELISA and three commercial enzyme immunoassays. The results are summarized in Table 1.

According to the algorithm established in this study (FIG. 2), a sample was considered negative if either no band or only one single band appeared, or if two or more bands appeared with a total score of less than or equal to 1; a sample was considered positive when at least two bands appeared with the sum of intensities higher than 2.5; if two or more bands appeared with a sum of intensities higher than 1 but less than or equal to 2.5 the sample was considered indeterminate if the antigen E line scored 0, and positive when the score of antigen E was higher than 0. A sample could not be interpreted when the streptavidin control line showed a rating greater than or equal to 1.

A total of 460 sera (43.3%) were negative in all four screening assays. Of these, 458 (99.6%) were also negative in the INNO-LIA. One serum gave an indeterminate result, while another serum was INNO-LIA-positive. Fifty-four sera (5.1%) were classified as "likely negative," since they were found to be either negative in two of the screening assays and doubtful in the remaining assays, or positive in one but negative in the three remaining tests. Of the likely negative sera, the INNO-LIA was able to confirm 41 sera (75.9%) as negative, and 11 sera (20.4%) as INNO-LIA-positive. Two sera (3.7%) were INNO-LIA-indeterminate.

Thirty-eight sera (3.6%) were classified by the screening tests as "likely positive" (i.e., either positive in two tests and doubtful in two other tests, or positive in three tests and negative in one). Of these, the INNO-LIA confirmed 32 sera (84.2%) as positive, 2 (5.3%) as INNO-LIA-indeterminate, and 4 sera (10.5%) as INNO-LIA-negative. Of the 500 sera (47.1%) positive in all four screening assays, 499 sera (99.8%) were also positive in the INNO-LIA, and 1 serum was INNO-LIA-negative. However, based on the results obtained in the four screening assays, 10 sera (0.9%) were considered as being controversial (i.e., two tests positive, the other two tests negative). Of these sera, 4 were INNO-LIA-negative, 1 INNO-LIA-indeterminate, and 5 INNO-LIA-positive.

Table 2 shows typical reactivity-patterns of 57 serum samples (serial numbers 1 to 57 and corresponding serum are given in the identification columns) on the INNO-LIA Chagas. The peptides used in the INNO-LIA Chagas are indicated by the letters A to G (A=SEQ ID N° 1; B=SEQ ID 2; C=SEQ ID 3; D=SEQ ID 4; E=SEQ ID 5; F=SEQ ID 6; G=SEQ ID 7). The scores are given for each antigen line ranging from 0 to 4 (see columns 4 to 10 and see also Examples section). The final interpretation is compared with the number of positive results (0 to 4, screening column) obtained by analysing the same sera with four different screening assays as indicated-above.

These data clearly demonstrate that the results obtained with the INNO-LIA Chagas assay help in establishing a confirmation and give additional information to the results obtained after subsequent usage of 4 different immunoassays.

Out of 1062 sera tested, 6 (0.6%) were INNO-LIA-indeterminate. One serum (PB 140) was negative in all supplemental assays. The remaining 5 sera reacted positive or doubtful in at least one of the supplemental assays. None of these samples were tested using PCR. Finally, 1 sample was INNO-LIA-positive/ELISA-negative (negative in all supplemental assays), and 1 sample was INNO-LIA-negative/LISA-positive (positive in 2 supplemental assays). None of these samples were tested by PCR.

When considering the performance of the INNO-LIA for sera positive in all four screening assays, the test showed a sensitivity of 99.8% (true positives/true positives+false negatives; 499/499+1; 95% CI: 98.89–99.99) and a specificity of 99.8% (true negatives/true negatives+false positives; 458/458+1; 95% CI: 98.79–99.99), if INNO-LIA-indeterminate results are excluded.

Finally, of the 20 sera obtained from patients with visceral leishmaniasis, and the 20 from patients with tegumentary leishmaniasis, none of the sera were reactive on the INNO-LIA Chagas Ab assay. By contrast, all visceral leishmaniasis sera and 2 (10%) tegumentary leishmaniasis sera gave a positive reaction when tested in IFA on *T. cruzi* epimastigotes and 3 visceral leishmaniasis sera and 1 tegumentary leishmaniasis serum were either indeterminate or positive in the Abbott Chagas antibody EIA.

Taken together, the present example illustrates the evaluation of a novel assay designed for the detection of IgG antibodies against *T. cruzi* in sera of patients with Chagas' disease which is intended to be preferentially used for the confirmation of results obtained by other serologic assays in routine diagnosis and blood bank screening. The interpretation algorithm was established based on the subset of samples either positive or negative in four different screening assays. Using serum panels obtained in four different endemic Brazilian regions, the INNO-LIA Chagas Ab showed a sensitivity of 99.8% (95% CI: 98.89–99.99) and a specificity of 99.8% (95% CI: 98.79–99.99) for sera with matched results in 4 different ELISA screening tests. Additional samples are being analysed by an independent laboratory as a validation set of sera.

An important feature of the INNO-LIA Chagas Ab is the utilization of seven different recombinant and synthetic peptide antigens that are coated as separate lines onto a reinforced membrane. As such, the assay can simultaneously check the sera for the presence of a broad spectrum of *T. cruzi*-specific antibodies which can bind to their respective antigens without steric hindrance. Such interference has been known to occur when a mixture of antigens is used to sensitize microwells, since the different molecules are tightly packed together in a limited physical space, thereby resulting in a loss of assay sensitivity.

Pastini et al. (1994) recently reported the development of the Dia Kit™ Bio-Chagas assay (Gador S. A., Buenos Aires, Argentina). This test employs 5 recombinant *T. cruzi* antigens expressed as glutathione S-transferase fusion proteins. A mixture of the antigens is coated as a single line onto a reinforced nitrocellulose membrane, together with a second human IgG control line to monitor the conjugate and subsequent color development steps. The authors found a sensitivity of 99.6% and a specificity of 99.1% upon assessment of 300 positive and 350 negative sera (matched IHA, IFA and ELISA results). However, the kit gave a positive result for 4 out of 16 sera obtained from patients with visceral leishmaniasis. In our study, the INNO-LIA Chagas Ab showed no reactivity to 20 sera from patients with visceral, and 20 sera from patients with tegumentary leishmaniasis. This indicates that the INNO-LIA will not provide false-positive results caused by cross-reactive Leishmania-specific antibodies.

Analysis of the data obtained in the present study showed that all sera with either indeterminate INNO-LIA results or INNO-LIA results which conflicted with the screening assay classification originate from Paraiba and the Amazon (Table 2, numbers 24, 29, 49, 54). These regions are known to be problematic in terms of Chagas' disease serology, since patients from these areas present low serologic titers against *T. cruzi* and are mostly asymptomatic. Xenodiagnosis and PCR studies carried out in Paraiba showed that the parasitemia in chronic patients is extremely low, thus providing an acceptable explanation to the low antibody titer. Moreover, the Amazon region is known to be co-endemic for *T. rangeli* which can lead to false-positive results in screening assays for antibodies to *T. cruzi* (Salles et al., 1996).

Only 1 serum gave a possibly false-negative reaction in the INNO-LIA, and 1 sample gave a possibly false-positive result (see Table 1). The possibly false-positive serum was negative in all four screening assays. However, the negative result by screening assays could be due to lack of sensitivity. Typically, within the setting of blood bank screening, such sample would not be subjected to confirmation. The possibly false-negative serum was positive in the four screening assays and in IFA and WB. If the INNO-LIA were used as a confirmatory test, this serum would not be considered as positive for Chagas antibodies. However, since the sample was obtained in the Amazon region, the possibility of a *T. rangeli* and/or Leishmania infections cannot be ruled out completely. Antibodies against these parasites could give false-positive results in the four screening assays as well as in WB and IFA, inasmuch as all these tests employ either crude or fractionated parasite antigen preparations. Unfortunately, the PCR status of these samples was unknown so that a more definitive conclusion concerning these samples could not be established.

In conclusion, the results presented in this study show that the INNO-LIA is a reliable confirmatory assay in the serodiagnosis of Chagas' disease with the potential to discriminate false-positive results caused by either *T. rangeli* or Leishmania infection.

REFERENCES

Almeida E C, Krieger M A, Carvalho M R et al. Use of recombinant antigens for the diagnosis of Chagas' disease and blood bank screening. Mem. Inst. Oswaldo Cruz. 1990;85:513–7.

Atherton, Shepard. Solid phase peptide synthesis. 1989. Solid phase peptide synthesis. IRL Press, Oxford.

Borges-Pereira J. Doença de Chagas humana: Estudo da infecção crônica, morbidade e mortalidade em Virgem da Lapa, MG, Brasil (1976–1996) (Dissertation). Rio de Janeiro: Fundação Oswaldo Cruz. 1997, 197 p.

Burns J. M., Shreffer W. G., Rosman D. E. et al. Identification and synthesis of a major conserved antigenic epitope of *Trypansoma cruzi*. Proc. Natl. Acad. Sci. USA 1992;89:1239–1243.

Carvalho M R, Krieger M A, Almeida E C et al. Chagas' disease diagnosis: evaluation of several tests in blood bank screening. Transfusion. 1993;33:830–4.

Guevara A. G., Taibi A., Billaut-Mulot O. and Ouaissi A. *Trypanosoma cruzi*: a 6x histidine-fused Tc24 protein useful for the serological diagnosis of Chagas' disease. Med. Sci. Res. 1997;25:399–400.

Hoft D. F., Kim K. S., Otsu K et al. *Trypanosoma cruzi* expresses diverse repetitive protein antigens. Infect. Immun. 1989;57:1959–1967.

Houbenweyl. Methode der organischen chemie, vol. 15, I & II (ed. Wunch E). 1974.Thieme, Stuttgart. IRL Press, Oxford.

Kerner N, Liegeard P, Levin M J, and Hontebeyrie-Josckowicz M. *Trypanosoma cruzi*: antibodies to a MAP-like protein in chronic Chagas' disease cross-react with mammalian cytoskeleton. Exp. Parasitol. 1991;73:451–9.

Lafaille J. J., Linss J., Krieger M. A. et al. Structure and expression of two *Trypanosoma cruzi* genes encoding antigenic proteins bearing repetitive epitopes. Mol. Biochem. Parasitol. 1989;35:127–136.

Maniatis T, Fritsch E, Sambrook J. Molecular cloning: a laboratory manual. 1982. Cold Spring Harbor Laboratory Press, Cold Spring Harbor, N.Y.

Oelemann W. M. R et al. 1998. Submitted for publication.

Pastini A C, Iglesias S R, Carricarte V C et al. Immunoassay with recombinant *Trypanosoma cruzi* antigens potentially useful for screening donated blood and diagnosing Chagas' disease. Clin. Chem. 1994;40:1893–4.

Peralta J M, Teixeira M G M, Shreffler W G et al. Serodiagnosis of Chagas' disease by enzyme-linked immunosorbent assay using two synthetic peptides as antigens. J. Clin. Microbiol. 1994;32:971–4.

Pollevick G. D., Affranchino J. L., Frasch A. C. and Sanchez D. O. The complete sequence of a shed acute-phase antigen of *Trypanosoma cruzi*. Mol. Biochem. Parasitol. 1991 ;47:247–250.

Salles N A, Sabino E C, Cliquet M G et al. Risk of exposure to Chagas' disease among seroreactive Brazilian blood donors. Transfusion 1996;36:969–973.

Vergara U., Veloso C., Gonzales A. and Lorca M. Evaluation of an enzyme-linked immunosorbent assay for the diagnosis of Chagas' disease using synthetic peptides. Am. J. Trop. Med. Hyg. 1992;46:39–43.

Zingales B, Gruber A, Ramalho C B et al. Use of two recombinant proteins of Trypanosoma cruziin the serological diagnosis of Chagas' disease. Mem. Inst. Oswaldo Cruz. 1990;85:519–22.

Zrein M., Louwagie J., Boeykens H. et al. Assessment of a new immunoassay for serological confirmation and discrimination of human T-cell lymphotropic virus infection. Clin. Diagn. Lab. Immunol. 1998;5:45–49.

TABLE 1

Results of four different screening tests*

| INNO-LIA Chagas | Negative | Likely negative | Controversial | Likely positive | Positive | Total |
|---|---|---|---|---|---|---|
| Positive | 1 | 11 | 5 | 32 | 499 | 548 |
| Indeterminate | 1 | 2 | 1 | 2 | 0 | 6 |
| Negative | 458 | 41 | 4 | 4 | 1 | 508 |
| Total | 460 | 54 | 10 | 38 | 500 | 1062 |

*Likely negative: negative by two different tests and doubtful by the remaining tests or negative by three and positive by one test;
Likely positive: positive by two different tests and doubtful by the remaining tests or positive by three and negative by one test;
Controversial: positive by two tests and negative by two other tests.

TABLE 2

| | | INNO-LIA Chagas reactivity pattern | | | | | | | Results by: | |
|---|---|---|---|---|---|---|---|---|---|---|
| Identifications | Control | A | B | C | D | E | F | G | INNO-LIA | Screening |
| 1 AM 004.1 | 0 | 0.5 | 1 | 1 | 1 | 3 | 0 | 3 | Positive | 4 |
| 2 AM 027.2 | 0 | 1 | 0.5 | 0 | 1 | 2 | 1 | 3 | Positive | 4 |
| 3 VL 013 | 0 | 1 | 0.5 | 0 | 2 | 1 | 0 | 3 | Positive | 4 |
| 4 VL 014 | 0 | 1 | 2 | 0.5 | 3 | 4 | 0 | 4 | Positive | 4 |

TABLE 2-continued

| | | INNO-LIA Chagas reactivity pattern | | | | | | | Results by: | |
|---|---|---|---|---|---|---|---|---|---|---|
| | Identifications | Control | A | B | C | D | E | F | G | INNO-LIA | Screening |
| 5 | VL 015 | 0 | 2 | 4 | 1 | 3 | 4 | 2 | 3 | Positive | 4 |
| 6 | VL 016 | 0 | 1 | 0 | 0 | 2 | 2 | 0 | 3 | Positive | 4 |
| 7 | VL 017 | 0 | 1 | 1 | 0 | 0.5 | 3 | 0 | 2 | Positive | 4 |
| 8 | VL 018 | 0 | 0.5 | 1 | 0 | 4 | 3 | 0 | 3 | Positive | 4 |
| 9 | VL 019 | 0 | 0.5 | 0 | 0 | 2 | 3 | 1 | 2 | Positive | 4 |
| 10 | VL 020 | 0 | 1 | 2 | 0.5 | 0 | 1 | 0 | 3 | Positive | 4 |
| 11 | VL 021 | 0 | 2 | 1 | 0.5 | 1 | 3 | 0 | 3 | Positive | 4 |
| 14 | VL 034 | 0 | 0.5 | 1 | 0 | 3 | 4 | 1 | 4 | Positive | 4 |
| 15 | VL 035 | 0 | 2 | 2 | 0 | 0 | 1 | 2 | 3 | Positive | 4 |
| 16 | VL 036 | 0 | 0 | 2 | 0.5 | 0 | 4 | 0 | 4 | Positive | 4 |
| 17 | VL 037 | 0 | 1 | 0.5 | 0 | 2 | 3 | 1 | 1 | Positive | 4 |
| 18 | VL 040 | 0 | 1 | 2 | 0 | 3 | 3 | 0 | 3 | Positive | 4 |
| 19 | VL 041 | 0 | 1 | 2 | 0.5 | 3 | 3 | 1 | 1 | Positive | 4 |
| 20 | PB 098 | 0 | 0 | 1 | 0.5 | 0 | 0.5 | 0 | 1 | Positive | 3 |
| 21 | PB 127 | 0 | 0 | 0 | 0 | 0 | 1 | 0 | 1 | Positive | 3 |
| 22 | PB 155 | 0 | 0 | 0 | 0 | 0 | 3 | 0 | 2 | Positive | 3 |
| 23 | PB 218 | 0 | 0.5 | 0 | 0 | 0 | 1 | 0 | 2 | Positive | 3 |
| 24 | PB 226 | 0 | 0 | 0 | 0 | 0 | 0.5 | 0 | 0.5 | Negative | 3 |
| 25 | PB 285 | 0 | 0 | 3 | 1 | 0 | 0 | 0 | 0 | Positive | 3 |
| 26 | PB 286 | 0 | 0.5 | 0 | 0 | 0 | 2 | 0 | 0.5 | Positive | 3 |
| 27 | PB 292 | 0 | 0 | 1 | 0 | 0.5 | 0 | 0 | 1 | Positive | 3 |
| 28 | PB 343 | 0 | 0.5 | 2 | 0.5 | 2 | 2 | 2 | 2 | Positive | 3 |
| 29 | PB 363 | 0 | 0 | 0 | 0 | 0 | 0 | 0 | 0 | Negative | 3 |
| 30 | PB 061 | 0 | 0 | 0 | 0 | 0 | 2 | 0 | 0.5 | Positive | 2 |
| 31 | PB 093 | 0 | 0 | 0 | 0 | 0 | 2 | 0 | 2 | Positive | 2 |
| 33 | PB 148 | 0 | 0 | 0 | 0 | 0 | 0 | 0 | 2 | Negative | 2 |
| 36 | PB 437 | 0 | 0 | 2 | 0 | 0 | 0.5 | 0 | 3 | Positive | 2 |
| 37 | PI 8791 | 0 | 0 | 0.5 | 0 | 1 | 2 | 0 | 2 | Positive | 2 |
| 38 | PI 8857 | 0 | 0 | 0 | 0 | 0 | 0 | 0 | 0 | Negative | 2 |
| 39 | PI 8929 | 0 | 0.5 | 0 | 0 | 0 | 0 | 1 | 4 | Positive | 2 |
| 40 | PB 086 | 0 | 0 | 0 | 0 | 0 | 0 | 0 | 0 | Negative | 1 |
| 42 | PB 149 | 0 | 0 | 0 | 0 | 0 | 0 | 0 | 2 | Negative | 1 |
| 43 | PB 152 | 0 | 0 | 0 | 0 | 0 | 0 | 0 | 0 | Negative | 1 |
| 44 | PB 160 | 0 | 0 | 0 | 0 | 0 | 0 | 0 | 0 | Negative | 1 |
| 45 | PB 167 | 0 | 0 | 0 | 0 | 0 | 0 | 3 | 0 | Negative | 1 |
| 48 | PB 242 | 0 | 0 | 0 | 0 | 0 | 0 | 0 | 0 | Positive | 1 |
| 49 | PB 245 | 0 | 0.5 | 0 | 0 | 0.5 | 0 | 0 | 0.5 | Negative | 1 |
| 50 | PB 266 | 0 | 0 | 0 | 0 | 0 | 0 | 0 | 0 | Negative | 1 |
| 51 | PB 268 | 0 | 0 | 0 | 0 | 0 | 0 | 0 | 0 | Negative | 1 |
| 52 | PB 275 | 0 | 0 | 0 | 0 | 0 | 0 | 0 | 0 | Negative | 1 |
| 53 | PB 342 | 0 | 0 | 0 | 0 | 0 | 0 | 0 | 0 | Negative | 1 |
| 54 | PB 404 | 0 | 0 | 0 | 0 | 0 | 2 | 0 | 2 | Positive | 1 |
| 56 | AM 001.1 | 0 | 0 | 0 | 0 | 0 | 0 | 0 | 0 | Negative | 0 |
| 57 | AM 002.1 | 0 | 0 | 0 | 0 | 0 | 0 | 0 | 0 | Negative | 0 |

TABLE 3

| T. cruzi proteins | SEQ I.D. number | Amino-acids sequence (one-letter code) |
|---|---|---|
| Tc24 | 1 | MGACGSKGSTSDKGLASDKDGKKAKDRKEAWERIRQAIPREKTAEAKQRRIELFKKFDKNETGKLCYDEVHS GCLEVLKLDEFTPRVRDITKRAFDKARALGSKLENKGSEDFVEFLEFRLMLCYIYDFFELTVMFDEIDASGNMLV DEEELKRAVPKLEAWGAKVEDPAALFKELDKNGTGSVTFDEFAAWASAVKLDADGDPDNVPESA |
| CRA | 2 | VAEAEKQKAAEATKVAEAEKQKAAEAMK |
| FRA | 3 | MEQERRQLLEKDPRRNAREIAALE |
| TcD | 4 | GAEPKSAEPKPAEPKSAEPKP |
| MAP | 5 | ALPQEEQEDVGPRHVDPDHFRSTTQDAYRPVDPSAYKR |
| SAPA | 6 | DSTAHGTPSTPADSSAHSTPSTPA |
| Ag39 | 7 | PSPFGQAAAGDKPSPFGQAAAGDK |

What is claimed is:

1. A composition comprising at least 6 recombinant and/or synthetic peptides obtained from 6 different *Trypanosoma cruzi* antigens which bind to *Trypanosoma cruzi*-specific antibodies and do not bind to Leishmania-specific antibodies, wherein said peptides consist of the amino acid sequences selected from SEQ ID Nos: 1 to 7.

2. A composition consisting of 7 recombinant and/or synthetic peptides obtained from 7 different *Trypanosoma cruzi* antigens which bind to *Trypanosoma cruzi*-specific antibodies and do not bind to Leishmania-specific antibodies, wherein said peptides consist of the amino acid sequences, SEQ ID Nos: 1 to 7.

3. A diagnostic kit for detecting *T. cruzi* in a biological sample, comprising a composition according to claim 1.

4. The diagnostic kit according to claim 3 wherein said kit further comprises a detection reagent.

* * * * *

UNITED STATES PATENT AND TRADEMARK OFFICE
CERTIFICATE OF CORRECTION

PATENT NO.    : 6,458,922 B1
DATED         : October 1, 2002
INVENTOR(S)   : Maan Zrein It is certified that error appears in the above-identified patent and that said Letters Patent is hereby corrected as shown below:

Column 4,
Line 58, change "monoclonal VI antibody" to -- monoclonal anitbody --.

Column 5,
Line 24, change "WO 96129606" to -- WO 96/29606 --.

Column 6,
Line 9, change "3-0 deacylated" to -- 3-0-deacylated --.
Line 17, change "endotoin" to -- endotoxin --.
Line 19, change "TWEEN 80/ emulsion" to -- TWEEN 80 emulsion --.
Line 22, change "Worchester" to -- Worcester --.
Line 27, change "A vaccine composition 'will further'" to -- "A vaccine composition" will further --.
Line 29, change "aline" to -- saline --.
Line 39, change "(ISCOMS)" to -- (ISCOMS) . --

Column 9,
Line 50, change "was_negative" to -- was negative --.
Line 56, change "negative/LISA" to -- negative/ELISA --.

Column 10,
Line 44, change "patients_with" to -- patients with --.

Signed and Sealed this

Fourth Day of February, 2003

JAMES E. ROGAN
*Director of the United States Patent and Trademark Office*